(12) United States Patent
Dioum

(10) Patent No.: US 10,118,838 B2
(45) Date of Patent: Nov. 6, 2018

(54) PRODUCT FOR REMOVING POLLUTANTS FROM A FLUID, AND METHOD FOR PRODUCING SAME

(76) Inventor: Serigne Dioum, Orleans (FR)

( * ) Notice: Subject to any disclaimer, the term of this patent is extended or adjusted under 35 U.S.C. 154(b) by 1196 days.

(21) Appl. No.: 13/383,883

(22) PCT Filed: Jul. 13, 2010

(86) PCT No.: PCT/FR2010/051478
§ 371 (c)(1),
(2), (4) Date: Feb. 22, 2012

(87) PCT Pub. No.: WO2011/007097
PCT Pub. Date: Jan. 20, 2011

(65) Prior Publication Data
US 2012/0138526 A1    Jun. 7, 2012

(30) Foreign Application Priority Data

Jul. 13, 2009 (FR) ...................... 09 54861

(51) Int. Cl.
*B01D 39/00* (2006.01)
*C02F 1/28* (2006.01)
(Continued)

(52) U.S. Cl.
CPC .............. *C02F 1/288* (2013.01); *A01N 25/08* (2013.01); *A01N 25/34* (2013.01); *C23C 14/046* (2013.01);
(Continued)

(58) Field of Classification Search
None
See application file for complete search history.

(56) References Cited

U.S. PATENT DOCUMENTS 4,407,865 A    10/1983  Nice
4,463,031 A    7/1984   Someya
(Continued)

FOREIGN PATENT DOCUMENTS

AP  P/1999/001694  * 4/2003 ............... C02F 1/50
WO  98/50597       11/1998
(Continued)

OTHER PUBLICATIONS

Hallin et al., "Improved Ni Ohmic COntact on n-Type 4H-SiC", Journal of Electronic Materials, vol. 26, No. 3, 1997.*
(Continued)

*Primary Examiner* — Michael H. Wilson
*Assistant Examiner* — Katherine A Will
(74) *Attorney, Agent, or Firm* — Young & Thompson

(57) ABSTRACT

This product (10) for removing pollutants from a fluid includes, on the one hand, a porous body (12) having an outer and inner specific surface (14) and, on the other hand, a metallized layer (16), the thickness of which is at most nanoscale, covering at least part of the outer and inner specific surface (14) of the porous body (12). The metallized layer (16) includes at least a metal (Ag) bonded to the porous body (12) by chemical bonds (18) that result from the action of intramolecular forces. Further, the metallized layer (16) includes silicon (Si) also bonded to the porous body (12) by chemical bonds (18) resulting from the action of intramolecular forces.

18 Claims, 2 Drawing Sheets

Figure 1:
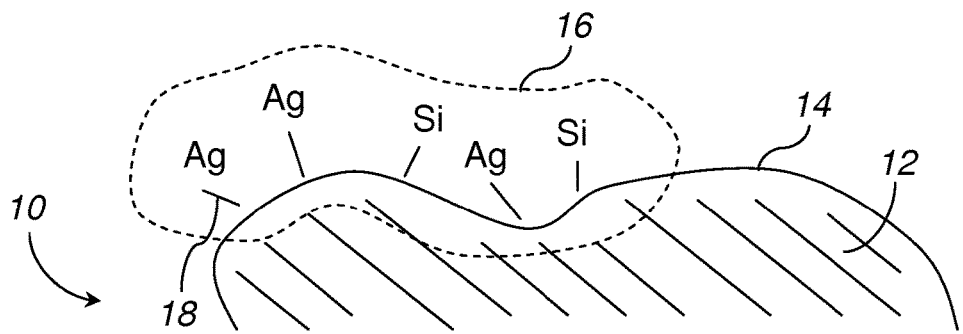

(51) Int. Cl.
*A01N 25/08* (2006.01)
*A01N 25/34* (2006.01)
*C23C 14/04* (2006.01)
*C23C 14/18* (2006.01)
*C23C 14/22* (2006.01)
*C02F 1/00* (2006.01)
*C02F 103/04* (2006.01)

(52) U.S. Cl.
CPC .......... *C23C 14/185* (2013.01); *C23C 14/223* (2013.01); *C02F 1/005* (2013.01); *C02F 1/283* (2013.01); *C02F 2103/04* (2013.01); *C02F 2201/006* (2013.01); *C02F 2301/046* (2013.01); *C02F 2303/04* (2013.01); *C02F 2305/08* (2013.01)

(56) References Cited

U.S. PATENT DOCUMENTS

| | | | | |
|---|---|---|---|---|
| 4,869,929 A | * | 9/1989 | Cabrera | ........ C23C 10/60 427/248.1 |
| 5,509,555 A | * | 4/1996 | Chiang | ........ C04B 35/573 216/101 |
| 6,197,120 B1 | | 3/2001 | David | |
| 6,878,419 B2 | * | 4/2005 | David | ........ B01D 67/0088 427/488 |
| 2005/0244313 A1 | | 11/2005 | Petrik | |
| 2011/0005461 A1 | * | 1/2011 | Vandermeulen | ...... C23C 16/511 118/723 MA |

FOREIGN PATENT DOCUMENTS

| | | | | |
|---|---|---|---|---|
| WO | WO 2005089112 A2 | * | 9/2005 | ............ A61K 48/00 |
| WO | WO2005089112 A2 | * | 9/2005 | ............ A61K 48/00 |
| WO | 2006/115486 | | 11/2006 | |
| WO | 2006/128187 | | 11/2006 | |

OTHER PUBLICATIONS

Pauling, Linus. (1970). General Chemistry (3rd Edition). Dover Publications, pp. 152-173.*

International Search Report dated Nov. 26, 2010, corresponding to PCT/FR2010/051478.

* cited by examiner

PRODUCT FOR REMOVING POLLUTANTS FROM A FLUID, AND METHOD FOR PRODUCING SAME

BACKGROUND OF THE INVENTION

Field of the Invention

This invention relates to a product for removing pollutants from a fluid. It also relates to a method for obtaining this product.

Description of the Related Art

Products for removing pollutants from water which act by filtration are well known. Activated carbon, sand or other porous bodies, for example, have a very good filtration capacity as a result of their large outer and inner specific surface that is very adsorbent. The main drawback of these products is that they have no bactericidal effect or even a bacteriostatic effect combined with their straightforward power to filter mechanically. On the contrary, they have been discovered to be the perfect harbouring place for bacteria and do not guarantee that the filtered water is potable. So chemical disinfectants (chlorine, peroxides, etc.) have to be added during the water treatment process.

Products for the bactericidal treatment of water are also well known, made up of activated carbon impregnated with silver in the form of salts. These treatment products are produced notably by immersion of the activated carbon into a solution of nitrates and other salts of silver. For example, information on a product of this type is given in the patent published under number FR 2 585 694. The drawbacks of this product are caused by salting out of silver and nitrates into the treated water which is inevitable. Nitrates remain present in the obtained product, and the silver that has been added as part of the process is only bonded to the porous body by weak Van der Waals chemical bonds.

Moreover, in document FR 2 585 694 and also in the patent published under number U.S. Pat. No. 4,407,865, a metallizing of activated carbon is provided with metal silver, by heating, in an area with an inert atmosphere where a high vacuum is moreover eventually created. In this area, the silver is evaporated to allow it to penetrate the carbon. This process results in good diffusion of the silver in the carbon pores but the poor attachment of the silver to the carbon leads again to salting out of the silver into the treated water. Moreover, the obtained product is more friable and is worn out by the passage of water. This application does not give a stable product, and it is difficult to obtain the product industrially.

More recently, the introduction of nanotechnologies has given the prospect of developing nanomaterials or materials that have one or more constituents present on a nanometric scale, these materials or constituents of material having specific, remarkable properties that fit them specifically to applications notably the fight to protect the environment or remove pollutants. In the field of treating fluids and water in particular, research has come up with several developments as much in the field of filtration (ultrafiltration through new generation membranes) as in the field of bactericidal or at least bacteriostatic treatment of fluids or as in that of treatment by degradation of chemical pollutants notably by metallic nanoparticles.

For example, a filter which removes pesticides based on nanoparticle chemistry has been developed at the Chennai Institute of Technology (IIT). This application is a result of the observation that halogenated hydrocarbons such as carbon tetrachloride break down into metallic halides and amorphous carbon following reactions with gold and nanoparticles of silver. However, this filter has no bactericidal or bacteriostatic effect.

Another example is the NANO-FOTOCIDE™ (nanoparticie filtration) unit (brand name), for which the University of Hong Kong developed the technology, that bases its principles on the action of low energy ultraviolet rays and the activation of a dioxide of titanium, the surface of which acts as a catalyst in the presence of air or water to generate hydroxyl radicals which oxidise certain pollutants such as bacteria and viruses by obtaining products of these reactions, namely carbon dioxide and water. However, it will be noted that this reaction that produces carbon dioxide is not ideal at a time when there are efforts to reduce the emission of this greenhouse gas.

Finally, research is currently being conducted, notably at Rice University, Houston, USA, on bimetallic nanoparticles and their ability to degrade organic aromatics and pesticides contained in underground water by the action of an ultraviolet ray.

Moreover, today's methods of injecting metallic atoms onto porous bodies in a plasma environment are better controlled, and they give rise to products that do not produce metallic salting out thanks to the establishment of strong chemical bonds between injected metallic atoms and the specific surface of the porous body.

By 'strong chemical bond', this means all bonding involving a chemical bonding that results from the action of intramolecular forces: so covalent bonds (sharing of a cloud of electrons between two atoms), ionic bonds (transfer of at least one electron from one atom to another), or even bonds at one or several electrons' higher energy levels are in this category. In contrast, a weak chemical bond results from the action of intermolecular forces, in other words, forces of electrical interactions of weak intensity between atoms, molecules or crystals: notably Van der Waals type bonds are in this category wherein there is no electron shared between atoms.

SUMMARY OF THE INVENTION

Therefore the invention applies more particularly to a product of the aforementioned type comprising, on the one hand, a porous body having an outer and inner specific surface and, on the other hand, a metallized layer, the thickness of which is at most nanoscale, covering at least part of the outer and inner specific surface of the porous body, the metallized layer including at least a metal bonded to the porous body by chemical bonds resulting from the action of intramolecular forces.

Information on such a product is given in the patent published under number EP 0 979 212. This product has a porous body and a metallic layer that is uniformly spread over the entire outer and inner specific surface of the porous body, wherein the metal atoms are bonded to the outer and inner surface of the porous body by covalent bonds. The use of this product in treating a fluid such as water proves its potential bactericidal properties.

However, there may be a need for the invention of a product for removing pollutants from a fluid that improves the treatment of this fluid even more.

Therefore, an object of the invention is a product for removing pollutants from a fluid that comprises, on the one hand, a porous body with an outer and inner specific surface and, on the other hand, a metallized layer, the thickness of which is at most nanoscale, covering at least part of the outer and inner specific surface of the porous body, the metallized layer including at least a metal bonded to the porous body by chemical bonds resulting from the action of intramolecular forces, characterised in that the metallized layer further includes silicon also bonded to the porous body by chemical bonds resulting from the action of intramolecular forces.

It appears that the addition of silicon into the metallized layer bonded to the porous body by strong bonds conserves its bactericidal properties while giving the product unexpected new properties, notably as regards electromagnetic rays, transfer of energy to the treated fluid and energetic catalysis in the degradation process of chemical pollutants such as certain hydrocarbons and other pesticides.

Optionally, at least part of the silicon is also bonded to at least part of the metal of the metallizing layer by chemical bonds resulting from the action of intramolecular forces.

Also optionally, the porous body has a carbonaceous component and the metallized layer has, in interaction with the porous body, components that are carbides of metal silicides, notably revealed at an energy level approximately equal to 283 eV.

Also optionally, the metallized layer further includes components which have carbon, silicon and metal atoms bonded together by covalent type chemical bonds.

Also optionally, the porous body includes at least one element selected from the group consisting of carbon powder, graphite, activated carbon, sand and zeolite.

Also optionally, the metal includes at least one heavy metal whose atomic mass is greater than or equal to that of copper.

Also optionally, the metallized layer partially covers the outer and inner specific surface of the porous body by the formation of aggregates.

Another object of the invention is a method for obtaining a product for removing pollutants from a fluid which includes a step of treating a porous body that has an outer and inner specific surface in an inert gas plasma deposition reactor with radiofrequency discharge, by immersing the porous body into the plasma and injecting metal into the plasma, characterised in that the step of treating the porous body also comprises an injection of silicon into the plasma.

Also optionally, the deposition reactor is a diode reactor with an electrical power approximately equal to 10 kW, coupled to a RLC impedance matching-box and in which the excitation temperature of the plasma is brought to between 5000 K and 7000 K during the treatment step.

Also optionally, a method for obtaining a product for removing pollutants from a fluid according to this invention can further include a preliminary step of functionalizing the porous body in a low pressure fluidized bed reactor, notably between 5 and 500 Pa, with a cold inert gas plasma and with inductive discharge.

BRIEF DESCRIPTION OF THE CRANING FIGURES

Figure 2:
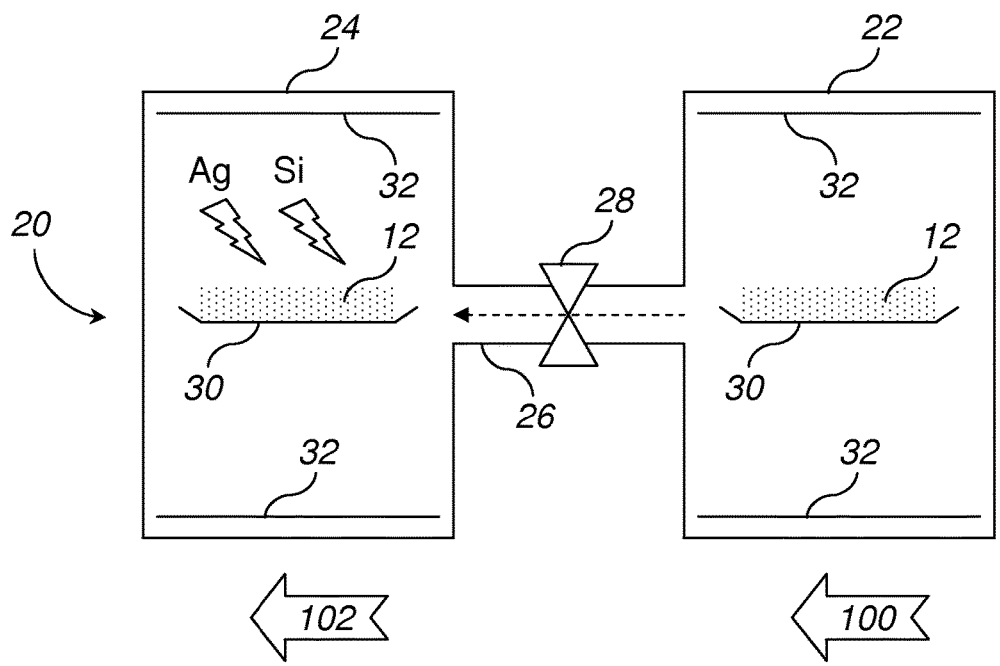
Figure 3:
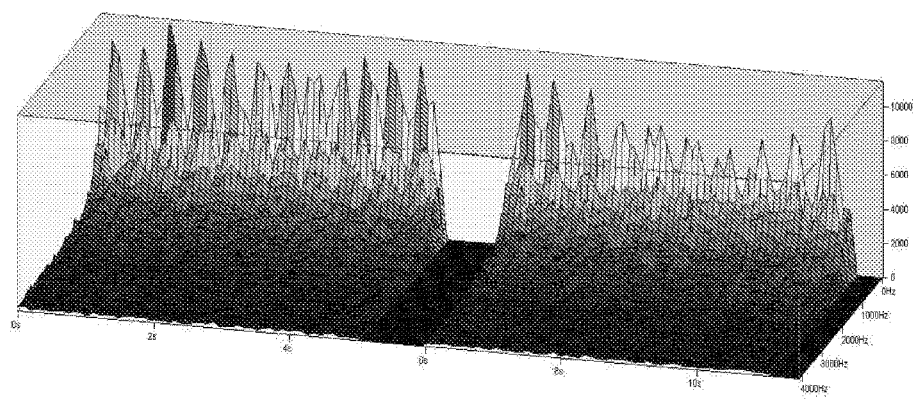
Figure 4:
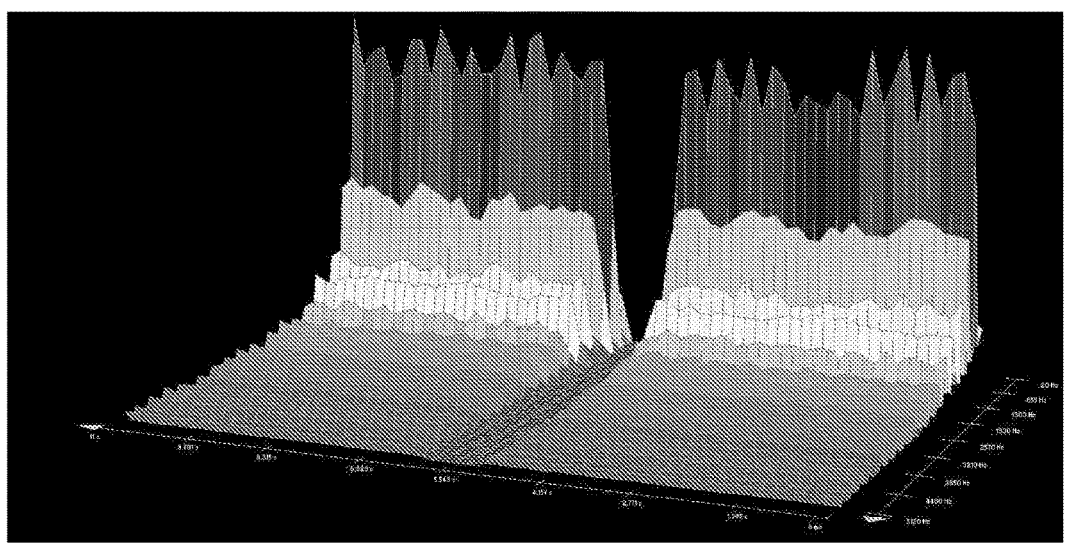

The invention will be better understood using the description that will follow, given only by way of example and referring to the drawing in the appendices in which:

FIG. 1 is a diagrammatic representation of the structure of a portion of product for removing pollutants from a fluid according to the invention, FIG. 2 is a diagrammatic representation of the general structure of an installation for the implementation of a method for obtaining the product of FIG. 1, and FIGS. 3 and 4 represent in diagrammatic form, measured energy levels of fluids which are either treated or untreated by a filtration unit that comprises a product according to the invention.

DETAILED DESCRIPTION OF THE INVENTION

The product 10 for removing pollutants from a fluid, represented partially and diagrammatically in FIG. 1 comprises a porous body 12 that has an outer and inner specific surface 14 of such an area that it provides a significant filtering power. In a preferred embodiment of the invention, the porous body includes a carbonaceous component such as carbon powder or granules of, for example, average granulometry of between 0.5 mm and 1 mm, graphite in sheets or bars, activated carbon, tissues or fibres of activated carbon or a combination of these parts. It can moreover include other components, notably components that have silicon in them such as sands or zeolite. Without any particular treatment, this porous body already has filtering properties, but not bactericidal or bacteriostatic ones.

Following a treatment such as that which will be detailed by referring to FIG. 2, the product 10 also has a metallized layer 16, the thickness of which is at most nanoscale, covering at least part of the outer and inner specific surface 14 of the porous body 12. By 'thickness of which is at most nanoscale', it is understood that the thickness never exceeds a few nanometers—it even stays mainly at less than a nanometer.

The metallized layer comprises metal, for example silver, but also silicon. The Ag and Si atoms of these components are bonded to the porous body 12 by strong chemical bonds, that is to say, in accordance with the definition which has been given above, by chemical bonds resulting from the action of intramolecular forces. Certain silver Ag and silicon Si atoms in the metallized layer 16 can also be bonded to each other by chemical bonds resulting from the action of intramolecular forces.

The product illustrated in FIG. 1, just given as one not limited example, has a layer that is metallized with silver but all other heavy metal or combination of heavy metals (bimetals, for example), notably including gold, copper and zinc, are equally feasible. More generally, by 'heavy metal' is understood all metals of atomic mass greater or equal to that of copper. Nickel will also work: the latter is generally considered as allergenic and carcinogenic, but in product 10 it would be present in such a minute quantity that it would not have these harmful effects.

Set up in this way, product 10 is mainly composed of carbon and a very small quantity of silicon and of heavy metal that is preferably present in a very pure form. The purity of the metal is for example in the order of N6, that is to say equal to 99.9999%. Moreover, the method for obtaining this product which will be given in detail by referring to FIG. 2 allows the deposition of a metallized layer with strong chemical bonds including the metal in an unoxidized form ($Ag^0$ form if silver is used).

This silverized layer with strong chemical bonds between the silver, the silicon and the porous body confers a bactericidal property on product 10 by energetic catalysis of oxidation reactions, or at least a bacteriostatic property.

By applying the method for obtaining the product that will be described by referring to FIG. 2, the metallized layer 16 has the advantage of comprising components that are carbides of metal silicides in interaction with the porous body 12, that are notably revealed at an energy level approximately equal to 283 eV. Production of these components that have a very stable molecular structure and are therefore solid and strong indicates that the chemical bonds between the metal, the silicon and the porous body (notably the carbon part of the porous body) are very strong, more particularly they are stronger than covalent or ionic bonds. So, product 10 does not risk losing one of its constituent parts when used to treat a fluid such as water for example and, since there is no risk of salting-out of nanoparticles even though its metallized layer is a thickness of which is at most nanoscale, it is adapted to applications that make water potable and related to other agro-alimentary industrial processes that require purification of fluids.

The metallized layer 16 can moreover have components that include carbon, silicon and metal atoms bonded together by covalent chemical bonds.

Finally, in a preferred embodiment, the metallized layer 16 only partially covers the outer and inner specific surface 14 of the porous body 12 by forming aggregates. In this way, the pores (notably micro pores) of the porous body, where the active sites can take part in ionic exchanges, adsorption and catalytic reactions, are not completely blocked by the metallized layer 16.

The installation 20 represented in FIG. 2 is adapted to the implementation of a method for obtaining the product 10 described above. The illustration is only diagrammatic and is not to scale.

It comprises a first functionalization plasma-enhanced reactor 22 linked to a second off-balance deposition reactor 24 by plasma, using a duct 26 that has a transfer system that comprises notably a gate 28. The control of this transfer system and of this gate 28 allows a plate 30 to pass from the interior of the first reactor 22 to the interior of the second reactor 24. In each reactor, a plasma environment is generated between electrodes 32 and the porous body 12, placed on the plate 30, is immerged in the plasma.

More precisely, using a method for obtaining product 10, during a first functionalizing step 100, the porous body 12 is immerged in the plasma of the first reactor 22. Reactor 22 has a low pressure fluidized bed, preferably a pressure between 5 Pa and 500 Pa, with a cold inert gas plasma and with an inductive discharge. The inert gas used can be, for example, argon. During this first step 100, the porous body 12 is bombarded with argon ions, the first effect of which is to get rid of impurities but it also develops the active surface by increasing its outer and inner specific surface and creating anchoring sites.

The parameters for functioning at step 100 could be as follows:
flow of argon: variable and dependant on the type of material used,
pressure in the reactor: between 5 Pa and 500 Pa,
temperature in the reactor: classic temperature in a cold plasma environment,
excitation power of the plasma: between 100 W and 400 W, for example 400 W, and
duration of the functionalizing step: 5 minutes.

During a second deposition step 102, the porous body 12 is immerged into the plasma of the second reactor 24, for example by opening gate 28 and controlling the transfer system, that is to say by moving plate 30 across duct 26. Reactor 24 is a diode reactor, with electrical power approximately equal to 10 kW, coupled to a RLC impedance matching-box, with a warm, inert gas plasma and radiofrequency discharge. The inert gas used can be for example argon. Deposition reactor 24 further comprises sources of silver and silicon. The source of silver can be for example one or several wires of silver, or a plate or sheet of silver, of dimensions that do not disturb the plasma environment generated in reactor 24. The source of silicon can be for example a plate or piece of quartz that is of a size and form also chosen not to disturb the plasma environment.

Alternatively, the source of silicon could come from the porous body itself, if it contains silicon, notably when it comprises sand or zeolite. For example, the porous body can be made up of a combination of activated carbon and zeolite. Zeolite is, from the point of view of its complex structure, an inorganic, crystalline polymer based on a series of tri-dimensional structures quadri-connected to tetrahedral $AlO_4$ and $SiO_4$ bonded together by an exchange of oxygen ions. The functionalizing step 100, when using such a combination, results in carbon macro pores being joined to regular zeolite micro pores by covering them in a thin layer. The carbon macro pores give ease access to the zeolite micro pores where the active sites can take part in ionic exchanges and in adsorption and catalytic reactions.

During the second step 102, the sources of silver and silicon are bombarded with argon ions in a plasma temperature of between 5000 K and 7000 K, which results in an injection of silver and silicon atoms in the argon plasma, on at least part of the outer and inner specific surface of the porous body 12 so that a metallized layer is formed, the thickness of which is at most nanoscale, and this metallized layer is bonded to the porous body by a formation of carbides of silver silicides and of by-products bonded covalently which combine carbon, silver and silicon. This layer is advantageously in aggregate form and does not block the pores of the porous body 12, even if it is possible to adjust the treatment parameters of step 102 to produce a more uniform layer. The duration of this step 102 can be varied but it is advantageous if less than 5 minutes is taken to produce a metallized layer in the form of aggregates, the thickness of which is at most nanoscale. The space between the electrodes 32 in the second reactor 24 can be, for example, about 4 cm so that a very high electric field can be established in the plasma. This creates a great modularity of the intensity of the flux of argon ions and provides optimum functionalization of the surface of the porous body 12. This second step 102 also allows the active surface of product 10 to develop by increasing the outer and inner specific surface.

The parameters for functioning at step 102 could be as follows:
flow of argon: about 40 scam (cm3 per minute),
pressure in the reactor: about 0.01 Pa,
plasma excitation temperature in the reactor: between 5000 K and 7000 K, mainly around 6000 K,
plasma excitation power: 1.5 kW,
frequency of the radiofrequency discharge: 13.56 MHz,
auto polarisation voltage: at least $1.2 \times 10^5$ V/m,
duration of the deposition step: 3 minutes, and
thickness of deposit: between 5 and 10 angstrom.

In these conditions, a high density of argon atoms is produced in the metastable excitation state $^3P_2$ and this confers a large amount of de-excitation energy on contact with the porous body 12. The rate of injected material is evaluated at 7.5 µg/s.

The X-ray photoelectron spectroscopy characterization of obtained product 10 allows notably the revelation of the energy peak of carbide of silver silicide at 283 eV, and also other bond energies relative to carbon, silicon and silver as well as other different oxidised states in very small quantities which benefit the chemical cleanup mechanisms and other oxidations of bacteria and viruses that are come across in the treatment of fluids.

Product 10 which is produced according to the invention and functionalized by one and the same integrated method such as the one described above, with a material such as activated carbon, has been tested and analysed for treating water. It appears that the bactericidal treatment is well proved and also the catalysis of the process of degradation of chemical pollutants such as certain hydrocarbons and other pesticides, such as DDT (dichlorodiphenyltrichloroethane), for example. Moreover, it is observed that the presence of silicon in the form of carbide develops the electric properties of the product.

Experimental Conditions of the Test

A filtration unit that has a first thickness filter and a second carbon filter comprising the treatment product 10 was installed in a laboratory to determine its effectiveness in the control of a certain number of human pathogens contained in water. The unit was set to work in a class III biological safety module using untreated water from the Thames as a source of water.

The precise items of equipment used for the test were as follows:
class III microbiological safety cabinet,
WATSON-MARLOW™ (pumping equipment) 800 series pump (brand name),
pressurised tubes,
50 liters of water from the Thames,
two sterile, 50 liter NALGENE® (polycarbonate) (brand name) containers,
first thickness filter (0.2μ),
carbon filter comprising product 10,
agar (BCYE, YEA) on plates.

The following microorganisms were used:
*Pseudomonas diminuta*: one of the smallest aquatic bacteria, often used to test filters because it is the organism that is most likely to penetrate a filtration system,
*Escherichia coli*: a particularly important indicator of faecal contamination
*Pseudomonas aeruginosa*: an opportunist bacteria in immuno-deficient patients,
*Legionella pneumophila* serogroup 1 Pontiac: a bacterial agent responsible for Legionnaire's disease, which multiplies in the hot and cold water systems of buildings as well as in cooling chimneys, and
*Cryptosporidium parvum*: a protozoan parasite that constitutes a major problem for the water industry because of its resistance to chlorine, the most commonly used disinfectant.

The microbial source was cultivated on a suitable agar breeding ground incubated at 37° C. for one night, then added separately to the test water to obtain an inoculation of between $10^2$ to $10^6$ per ml for each microorganism. *Cryptosporidium parvum* was added to obtain a quantity of between $10^4$ to $10^5$ per ml.

A circulation loop was used on the filter unit for at least thirty minutes to condition the unit before proceeding with the test. Water containing the inoculation of bacteria was then introduced into the filter at a rate of 4.15 l/min so that the efficiency of the filtration unit in reducing the bacterial load could be determined.

Dilutions in series from the first filter were used to determine the effective number of bacteria (colonies forming units per ml) entering and passing through the filtration unit.

Samples of filtered water (100 ml) have been concentrated by filtration.

The samples have been cultivated on a breeding ground of BCYE agar for the analysis of *Legionella*. Samples of *Pseudomonas diminuta, Pseudomonas aeruginosa* and *Escherichia coli* have been cultivated on appropriate agar breeding grounds (YEA).

A sample of post-filtration water from each test was preserved and recultivated 15 days later to determine whether redevelopment had taken place.

An aliquot (10 ml) of post-filtration water was mixed immediately with 10 ml of pre-filtration water and the number of organisms that could be cultivated immediately was determined after 5 minutes and after 15 days.

The percentage of viable oocytes of *Cryptosporidium parvum* in both pre- and post-filtration water was determined by determining vital contamination by using propidium and 4'-6' diamidino 2-phenylindole. The results were obtained by microscopic examination, using a fluorescent microscope.

The number of viable *Cryptosporidium parvum* oocytes in ml in the samples of pre- and post-treatment water was determined by using *Cryptosporidium* monoclonal antibody contamination. These antibodies were marked by the fluorescence.

Finally, the equipment was fumigated with formaldehyde and warm water (60° C.) was passed inside the filtration unit to deactivate *Cryptosporidium parvum*.

Test Results and Discussion

The tested filtration unit removed more than 99.9% of all species of bacteria tested. There was a reduction of 100% in the number of *Escherichia coli* and *Legionella pneumophila*, and no bacteria at all were found after treatment. It was found that this was confirmed when 100 ml of post-filtration water was concentrated and analysed for the presence of bacteria. Merely by putting water through the filtration unit at a rate of 4.15 l/min using water from the Thames suggests that this filtration unit would reduce the presence of pathogenic bacteria contained in the water by more than 99.9%.

The samples of post-filtration water were preserved for 15 days and proved that no redevelopment took place in the samples of filtered water.

Bacteria were added to the post-filtration water to determine the residual bactericidal effectiveness. The results indicate that a reduction of 10% to 20% was obtained within 5 minutes. However, after 15 days, a reduction greater than 95% was noted. The results indicate that the post-filtration water would not be able to overcome quickly any re-contamination by the bacteria used in this test.

The protozoan *Cryptosporidium parvum* is particularly resistant to treatment by disinfectants. However, there was a notable reduction (more than 95%) on the number of *Cryptosporidium parvum* passing through the filtration unit.

It will be noted moreover, that this test reveals the decontaminating properties of the filtration unit comprising product 10 and also the very singular property of the remanence of the decontamination treatment. Remanence can be defined as the persistence of a phenomenon when the cause of this phenomenon has disappeared. In the case of the tested bactericidal treatment, the treated fluid conserves (sometimes for several weeks according to the experimental conditions) its decontaminating power that ensures cleanliness of the water is maintained without the addition of any supplementary chemical product at all such as chlorine or any other. The study and characterization of this remanence leads to the determination of the different parameters which influence the treatment procedure to be used such as the kinetic energy of water going through the filtration unit, its mineral content, etc.

Moreover, by looking at the parameter of the temperature of the water before and after treatment by the filtration unit, the endothermic character of the catalytic reactions after treatment can be shown since untreated water initially at 26° C. with an ambient temperature of 27° C. comes out of the filtration unit at 18° C. and remains constant at 19° C. several hours later even when left in fresh air in the same environment at constant ambient temperature, which brings into effect a positive variation in enthalpy.

Finally, observation of electrostatic phenomena associated with product 10 leads to interest in undertaking a study of the dynamics of the electric fields, very weak in the treated fluids, by using an apparatus such as the 'BIOSCOPE™ (electric field analyzer) System' (brand name) marketed by the SONOSCOPE™ (ultrasound detector) company. The principle upon which this apparatus works is based on the electro-bio-impedance and the apparatus detects and registers subtle variations in the electro-acoustic fields common to all bioactive environments. The apparatus generates a reference signal at non-acoustic audio frequency and this signal is used to regulate an extendable electric field. This reference signal is transmitted via a transducer electrode to the sample to be analysed. A reference signal is established between the apparatus and the sample which is digitized. When a material is in contact with the environment, it causes disturbance that in its turn modifies the reference signal.

This apparatus displays subtle state variations which cannot be detected by chemical analysis. It can therefore display very quickly the changes in parameters including changes in quality and possible contamination of the treated water.

FIG. 3 illustrates using a diagram, the clear difference in energy levels between water treated by the product 10 (diagram on the left) and the same water when untreated (diagram on the right) at the same excitation frequency (281.25 Hz) and with an identical exit flow. This diagram gives the development over time of the spectrum of a wave sent by the corresponding environment (treated water on the left and untreated water on the right) between 0 Hz and 4000 Hz in response to the excitation wave.

Moreover, the electromagnetic effects and therefore the energetic effects of product 10 affect the treated fluid even when the latter is not directly in contact with the product as the following spectra show in FIG. 4. In this figure, the energy differences between water treated by product 10 (diagram on the left) and the same water when untreated (diagram on the right) but taken out from close proximity to the filtration unit comprising product 10, are clearly less significant.

The observed electrostatic phenomena are verified in this way, and they show that the tested filtration unit has an effect of increasing the force of exciting the fluid to be treated, even without direct contact when the fluid remains in close proximity to product 10. These electrical properties stem from the presence of carbide of metal silicide.

This energetic dynamics has effects on a cellular level, when different amounts of water are introduced into a cellular breeding ground and when the absorbance of protein is measured. Indeed, a study comparing the effect of untreated water and the same water treated using product 10 was completed on breeding grounds of fibroblasts (between 20% and 50% in the breeding ground). Measurements were taken in the supernatants after 48 hours of treatment. The result is that the introduction of treated water using product 10 can be increased to over 50% in proportion of to the breeding ground, whereas untreated water cannot reach 10% without cells dying. Since increasing the proportion of water weakens the nutritive breeding ground, it is thus obvious that the bioavailability of the breeding ground is clearly improved with treated water. The effect of this is that it is noted that there is better cellular growth with treated water.

It appears clearly that a product for removing pollutants according to the invention, and in particular the one described and tested previously, has good catalytic power in bactericidal reactions of fluids such as water, air or other industrial fluids. As the completed tests show, it has moreover astonishing properties of remanence for several weeks of the bactericidal effect on, and of improvement of bioavailability of, the treated fluid, by increasing the force of notably, its energy. Finally, it produces an effect on the fluid by electromagnetic rays, from a distance, without direct contact.

The method for obtaining this product for removing pollutants described with reference to FIG. 2 can allow considerable increase in the size of the specific surface of the final product, therefore improving its capacity for adsorption and therefore for filtration, as has been specified in the description of the functionalizing and deposition steps 100 and 102.

Moreover, it will be noted that the invention is not limited to the previously described embodiment. Other metals, notably heavy metals other than silver, can be used to metallize the layer, the thickness of which is at most nanoscale.

More generally, as is known to whose skilled in the art, there are various modifications that can be made to the embodiment described above, with respect to the instruction that has been disclosed. In the following claims, the terms used should not be interpreted as limiting the claims to the embodiment presented in this description, but should be interpreted to include all the equivalents that the claims intend to cover by their formulation and whose project is within reach of those skilled in the art by applying their general knowledge to the instruction that has just been disclosed.

The invention claimed is:

1. A product for removing bacteria from a fluid, comprising:
   a porous body comprising a carbonaceous component and having an outer and inner specific surface; and
   a metallized layer a thickness of which never exceeds a few nanometers, covering at least part of the outer and inner specific surface of the porous body, the metallized layer including at least a metal bonded to the porous body by chemical bonds resulting from the action of intramolecular forces,
   wherein the metallized layer further includes silicon also bonded to the porous body by chemical bonds resulting from the action of intramolecular forces, and
   the metallized layer comprises, in interaction with the porous body, components that are carbides of metal silicides with chemical bonds between their carbon, metal and silicon atoms that result from the action of intramolecular forces, wherein the metal silicides are silver silicides or silicides of a metal whose atomic mass is greater than or equal to that of copper obtained by immersing the porous body into the plasma of an inert gas plasma deposition reactor with radiofrequency discharge and injecting metal and silicon into the plasma.

2. The product for removing bacteria from a fluid as claimed in claim 1, wherein at least part of the silicon is also bonded to at least part of the metal of the metallized layer by chemical bonds resulting from the action of intramolecular forces.

3. The product for removing bacteria from a fluid as claimed in claim 2, wherein said carbides of metal silicides are components that are revealed at an energy level approximately equal to 283 eV.

4. The product for removing bacteria from a fluid as claimed in claim 1, wherein said carbides of metal silicides are components that are revealed at an energy level approximately equal to 283 eV.

5. The product for removing bacteria from a fluid as claimed in claim 4, wherein the metallized layer further comprises components including carbon, silicon and metal atoms bonded together by covalent bonds.

6. The product for removing bacteria from a fluid as claimed in claim 4, wherein the porous body includes at least one element selected from the group consisting of carbon powder, graphite, activated carbon, sand and zeolite.

7. The product for removing bacteria from a fluid as claimed in claim 4, wherein the metallized layer partially covers the outer and inner specific surface of the porous body by the formation of aggregates.

8. The product for removing bacteria from a fluid as claimed in claim 1, wherein the porous body includes at least one element selected from the group consisting of carbon powder, graphite, activated carbon, sand and zeolite.

9. The product for removing bacteria from a fluid as claimed in claim 1, wherein the metallized layer partially covers the outer and inner specific surface of the porous body by the formation of aggregates.

10. The product for removing bacteria from a fluid as claimed in claim 1, wherein the product does not lose constituent parts when treating water.

11. The product for removing bacteria from a fluid as claimed in claim 1, wherein the product does not salt out nanoparticles when treating water.

12. A method for obtaining a product for removing bacteria from a fluid, comprising:
    treating a porous body comprising a carbonaceous component and having an outer and inner specific surface in an inert gas plasma deposition reactor with radiofrequency discharge, by immersing the porous body into the inert gas plasma with a source of metal; and
    injecting said metal into the inert gas plasma, on at least part of the outer and inner specific surface of the porous body by bombarding ions of plasma's inert gas on the source of metal, so as to form a metallized layer, a thickness of which never exceeds a few nanometers, covering at least part of the outer and inner specific surface of the porous body,
    wherein the step of treating the porous body also comprises immersing the porous body into the inert gas plasma with a source of silicon and injecting said silicon, in the inert gas plasma with the metal, on said at least part of the outer and inner specific surface of the porous body by bombarding ions of plasma's inert gas on the source of silicon, so that the metallized layer comprises, in interaction with the porous body, components that are carbides of metal silicides with chemical bonds between their carbon, metal and silicon atoms that result from the action of intramolecular forces, wherein the metal silicides are silver silicides or silicides of a metal whose atomic mass is greater than or equal to that of copper.

13. The method for obtaining a product for removing bacteria from a fluid as claimed in claim 12, wherein the deposition reactor is a diode reactor with electrical power approximately equal to 10 kW, coupled to a RLC impedance matching-box, and in which the excitation temperature of the plasma is brought to between 5000 K and 7000 K during the treatment step.

14. The method for obtaining a product for removing bacteria from a fluid as claimed in claim 12, further comprising a preliminary step of functionalizing the porous body in a low pressure fluidized bed reactor, of between 5 and 500 Pa, with a cold inert gas plasma and with inductive discharge.

15. The method for obtaining a product for removing bacteria from a fluid as claimed in claim 13, further comprising a preliminary step of functionalizing the porous body in a low pressure fluidized bed reactor, of between 5 and 500 Pa, with a cold inert gas plasma and with inductive discharge.

16. The method for obtaining a product for removing bacteria from a fluid as claimed in claim 12, wherein the product does not lose constituent parts when treating water.

17. The method for obtaining a product for removing bacteria from a fluid as claimed in claim 12, wherein the product does not salt out nanoparticles when treating water.

18. A product for removing *E. coli* from a fluid, comprising:
    a porous body comprising a carbonaceous component and having an outer and inner specific surface; and
    a metallized layer a thickness of which never exceeds a few nanometers, covering at least part of the outer and inner specific surface of the porous body, the metallized layer including at least a metal bonded to the porous body by chemical bonds resulting from the action of intramolecular forces,
    wherein the metallized layer further includes silicon also bonded to the porous body by chemical bonds resulting from the action of intramolecular forces, and
    the metallized layer comprises, in interaction with the porous body, components that are carbides of metal silicides with chemical bonds between their carbon, metal and silicon atoms that result from the action of intramolecular forces, wherein the metal silicides are silver silicides or silicides of a metal whose atomic mass is greater than or equal to that of copper obtained by immersing the porous body into the plasma of an inert gas plasma deposition reactor with radiofrequency discharge and injecting metal and silicon into the plasma.

* * * * *